(12) United States Patent
Delcourt (10) Patent No.: US 6,924,112 B1
(45) Date of Patent: Aug. 2, 2005

(54) CLONING METHOD BY MULTIPLE-DIGESTION, VECTORS FOR IMPLEMENTING SAME AND APPLICATIONS

(75) Inventor: Marc Delcourt, Paris (FR)

(73) Assignee: Biomethodes S.A.R.L., Paris (FR)

( * ) Notice: Subject to any disclaimer, the term of this patent is extended or adjusted under 35 U.S.C. 154(b) by 0 days.

(21) Appl. No.: 09/586,131

(22) Filed: Jun. 2, 2000

Related U.S. Application Data (63) Continuation of application No. PCT/FR98/02629, filed on Dec. 4, 1998.

(30) Foreign Application Priority Data

Dec. 4, 1997 (FR) .................................. 97 15319

(51) Int. Cl.[7] .......................... G01N 33/53; C12P 19/34
(52) U.S. Cl. ......................... 435/7.1; 435/6; 435/91.1; 435/91.4; 536/25.3
(58) Field of Search ................................ 435/6, 71, 7.1

(56) References Cited

U.S. PATENT DOCUMENTS 5,252,724 A    10/1993    Kishimoto et al.

FOREIGN PATENT DOCUMENTS

WO    WO 95/04745    2/1995

OTHER PUBLICATIONS

Piug Deng and Jac A. Nickoloff, Site-Directed Mutagenesis Of Virtually Any Plasmid By Eliminating A Unique Site.
Jones, et al, Production Of A Vector To FAcilitate DNA Mutagenesis and Recombination, Biotech, vol. 16, No. 4, 1994.
Amersham Life Science Catalogue, pp. 164-165 XP002076172.

*Primary Examiner*—Andrew J. Wang
*Assistant Examiner*—My-Chau T Tran
(74) *Attorney, Agent, or Firm*—Schnader Harrison Segal & Lewis LLP (57) ABSTRACT

The present invention pertains to a process for isolating an intact clone of one target nucleic acid fragment having a known characteristic, from a group of fragments by preparing an initial library of clones from the group of fragments using a vector containing no more than a predetermined number of known restriction sites, preferably 1–3 restriction sites, subjecting the initial library to at least 10, and preferably between 50 and 70 restriction enzymes different from those to which the vector is susceptible, to produce a group of monodigested libraries, screening the group of monodigested libraries for the target fragment to determine those restriction enzymes to which the target fragment is insensitive, and subjecting the initial library to substantially all of the restriction enzymes to which the target fragment is insensitive, to produce a multidigested library having an intact clone of the target nucleic acid fragment. The target fragment can then be separated, transfected, reproduced, and studied or sequenced.

18 Claims, 8 Drawing Sheets

Cellules non transfectées −

Cellules transfectées +

I　　　II　　　LXX

Fig.8

Digestion par
II, III, V, VI, ...
... LXX.

Fig.9

Transformation

Culture

Un plasmide unique.

Fig.10

1: Extrait cellulaire de cellules non transfectées.
2: Extrait cellulaire de cellules transfectées par la banque totale.
3: Extrait cellulaire de cellules transfectées par la banque digérée par I.
4: Extrait cellulaire de cellules transfectées par la banque digérée par LXX.

Fig.11

CEM: $I^sI^rII^rIV^sV^rVI^r...LXIX^sLXX^r$.

<u>0</u>: Plasmide seul (clivé B)  <u>t</u>: Banque totale.
<u>1</u>: Banque clivée par I.  <u>2</u>: Banque clivée par II.

Fig.16

CEM: I$^s$II$^r$III$^r$IV$^r$V$^s$V$^r$VI$^r$...LXIX$^s$LXX$^r$.

Fig. 17

1: préparation d'ADN plasmidique de bactéries transformées par le plasmide seul.
2: préparation d'ADN plasmidique de bactéries transformées par la banque totale.
3: préparation d'ADN plasmidique de bactéries transformées par la banque digérée par I.
4: préparation d'ADN plasmidique de bactéries transformées par la banque digérée par LXX.

Fig. 18

CEM: I$^r$II$^r$III$^r$IV$^s$V$^r$VI$^r$...LXIX$^s$LXX$^r$.

Fig. 19

CEM:   A: I$^r$II$^s$III$^r$IV$^r$...
       B: I$^s$I$^r$III$^r$IV$^s$...
       C: I$^s$II$^r$III$^s$IV$^r$...

US 6,924,112 B1

CLONING METHOD BY MULTIPLE-DIGESTION, VECTORS FOR IMPLEMENTING SAME AND APPLICATIONS

This is a continuation of Application No. PCT/FR98/02629, filed Dec. 4, 1998.

FIELD OF THE INVENTION

The present invention pertains to the field of molecular biology and relates more specifically to the cloning of genes.

DESCRIPTION OF THE RELATED ART

Gene cloning is a rapidly expanding field that envisages especially the association of functions and genes. This field is developing primarily according to two major axes: that of reverse molecular biology, on the one hand, which consists of the large-scale sequencing of genomic or complementary DNA libraries, and of direct molecular biology, on the other hand, which consists of finding the sequence responsible for an observed activity, such as an enzymatic activity or a homology with other genes.

SUMMARY OF THE INVENTION

The present invention pertains to a process for isolating an intact clone of one target nucleic acid fragment having a known characteristic, from a group of fragments by preparing an initial library of clones from the group of fragments using a vector containing no more than a predetermined number of known restriction sites, preferably 1–3 restriction sites, subjecting the initial library to at least 10, and preferably between 50 and 70 restriction enzymes different from those to which the vector is susceptible, to produce a group of monodigested libraries, screening the group of monodigested libraries for the target fragment to determine those restriction enzymes to which the target fragment is insensitive, and subjecting the initial library to substantially all of the restriction enzymes to which the target fragment is insensitive, to produce a multidigested library having an intact clone of the target nucleic acid fragment. The target fragment can then be separated, transfected, reproduced, and studied or sequenced.

DETAILED DESCRIPTION OF THE INVENTION

The present invention is based precisely on providing a new method for cloning a fragment of nucleic acid, which method will be referred to below as DMD for "Differential Multiple Digestion", which is based on the systematic, combined and preparative use of the restriction sites present on the inserts constituting a library of complementary or genomic DNA.

DMD is applicable especially to the screening of expression or cloning libraries by homology.

The present invention also has applications in the time-consuming field of sequencing when it only has an insert identification activity, as well as in the study of human polymorphism, especially in the context of research focused on genetic predispositions.

The Enzymatic Characteristic (EC) will be designated below as the resistance, indicated by an "r", and the sensitivity, indicated by an "s", of a nucleic acid fragment to a restriction enzyme. Which means:

that a fragment classified as "s" for a given restriction enzyme contains the cleavage site of this enzyme, and that a fragment classified as "r" for a restriction enzyme does not contain the cleavage site of this enzyme.

The Multiple Enzymatic Characteristic (MEC) is thus the totality of the ECs obtained for a multiplicity of enzymes. Thus, the MEC of a DNA fragment containing an Eco site, a Bam site, two SCa sites, but no Hind or Stu sites can be represented in the following manner: $Eco^s Bam^s Sca^s Hind^r Stu^r$.

Thus, the process of the invention proposes associating the fragment that one is endeavoring to isolate within a sample with its multiple enzymatic characteristic (MEC). The search for said fragment can be performed by any means known by the expert in the field, such as its capacity to hybridize with a nucleic probe, the enzymatic expression of its protein product, the expression of a protein which can be detected, etc.

The cloning process according to the invention is based on the demonstration that when the number of enzymes is sufficiently large, each insert in the library has an original MEC, and therefore, the invention offers a simple strategy for cloning genes based on their MEC. The process according to the invention is thus based on scanning DNA libraries using in a combinatory manner the distribution of the restriction sites on the inserts constituting this library.

The principle of the process according to the invention is also based on the use of a vector of a type which is novel because it is substantially free of all of the cleavage sites for the restriction enzymes, only retaining those which are necessary for the construction of the oriented or nonoriented library, and for its possible subcloning in another vector. In a particularly minimal form of implementation, the vector contains:
  one site A necessary for construction of the library, and
  two sites B which are identical and flank the site A, which are useful for subcloning the gene once it has been identified and cloned.

Figure 1:
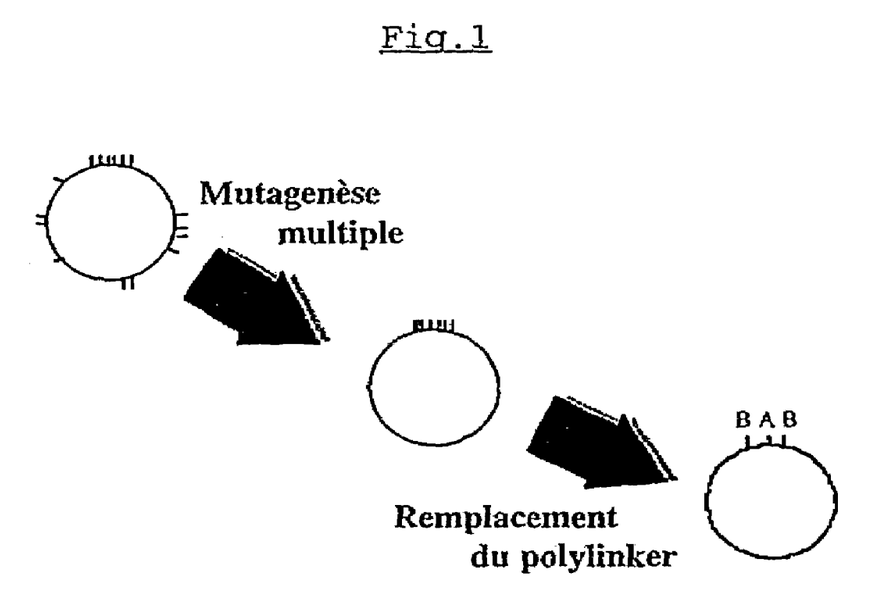
FIG. 1 is a schematic representation of the production of a "trilinker" vector.

This group can be designated below as "trilinker", the schematic fabrication of which is shown in attached FIG. 1.

In another specific form of implementation, the vector contains:
  one site A and one site A', which are different, for constructing the library, and
  two sites B and B', which are identical or different, and flank the sites A and A', for subcloning the gene once it has been identified and cloned.

The B sites are advantageously octonucleotidic sites, so as to minimize the risk that B sites would be present in the cloned inserts. It would thus be possible to easily subclone in a single piece.

Approximately 100 restriction enzymes with hexanucleotidic sites have been discovered to date. Of these, 70 have a continuous or discontinuous palindrome type recognition site.

A vector of the invention, advantageously a plasmid, no longer contains—with the exception of these three sites—hexanucleotidic or pentanucleotidic restriction sites corresponding to the restriction enzymes which have already been identified or will be identified in the future. It is understood that the term "substantially" indicates that this destruction can be partial in the sense that it only involves certain of the known sites; thus, only the corresponding enzymes will be used in the process of the invention. In the presentation of the invention below, it will be assumed, as previously indicated, that approximately 50 to 70 types of sites were destroyed.

A vector of the invention can be constructed from an already existing plasmid and possess all of the functions necessary to enable creation and manipulation of a complementary or genomic DNA library. It can be useful in the process of the invention if the library no longer contains any single self-closed vectors. It is thus advantageous if the vector of the invention contains a system which eliminates any single self-closed vectors such as a suicide gene, a lambda promoter proximity disruption system or any other system known by the expert in the field.

The technique used in the framework of the invention for destroying all of the restriction sites is one of the simple or multiple directed mutagenesis techniques already described in the prior art, or any other technique known by the expert in the field, such as the replacement of plasmid segments by oligonucleotides. One thereby obtains a vector which is resistant to 70 restriction enzymes, numbered from 1 to LXX, and sensitive to 2, which were previously designated as A and B. The idea of simultaneously destroying the majority of the restriction sites present on a plasmid was envisaged by D. H. Jones et al. (BioTechniques 1994, 16, 4: 694), but in a different context. In fact, this article describes the destruction by multiple mutagenesis of 31 of the 37 sites of a very small vector so as to create a new tool facilitating certain DNA manipulations.

The process of the invention is also based on the creation of a DNA library, which for the envisaged application contains from 1 to $10^8$, and preferably on the order of $10^5$ to $4 \cdot 10^6$ different fragments, each on the order of 0.1 kb to 5 kb, and preferably depending on the applications of the process of the invention, from 1 to 2 kb. In the particular mode of implementation of the invention described in example 6 below pertaining to the study of polymorphism, the library can comprise only a single fragment.

Figure 2:
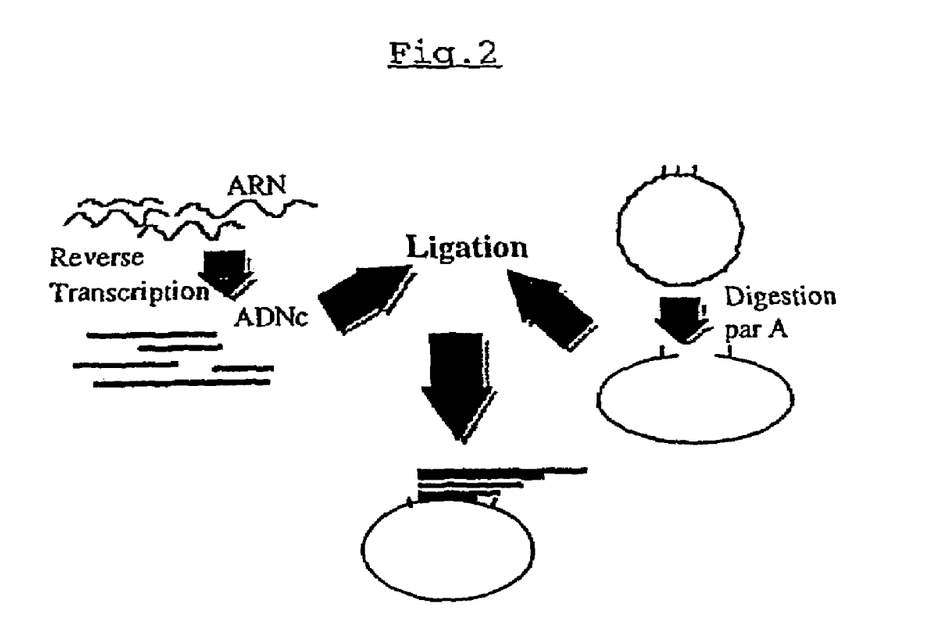
FIG. 2 is a schematic representation of the insertion of complementary DNA of a tissue or cell line of interest into site A of a vector.

Thus, for the application of the process of the invention to the fabrication of expression or cloning by homology libraries, there was prepared, as shown schematically in attached FIG. 2, a cDNA library of $10^5$ different fragments, each of 1 kb.

However, this model constitutes an approximation and is thus slightly false, since the size of the fragments is heterogeneous. Since the average size of the inserts was underestimated and the size of the library was overestimated, this model was selected so as to have available a simple base (homogeneity of the size of the fragments) and a test system which put analysis at a disadvantage (size of the library overestimated, size of the fragments underestimated) in a manner such that the process of the invention would be reproducible in all cases.

Figure 3:
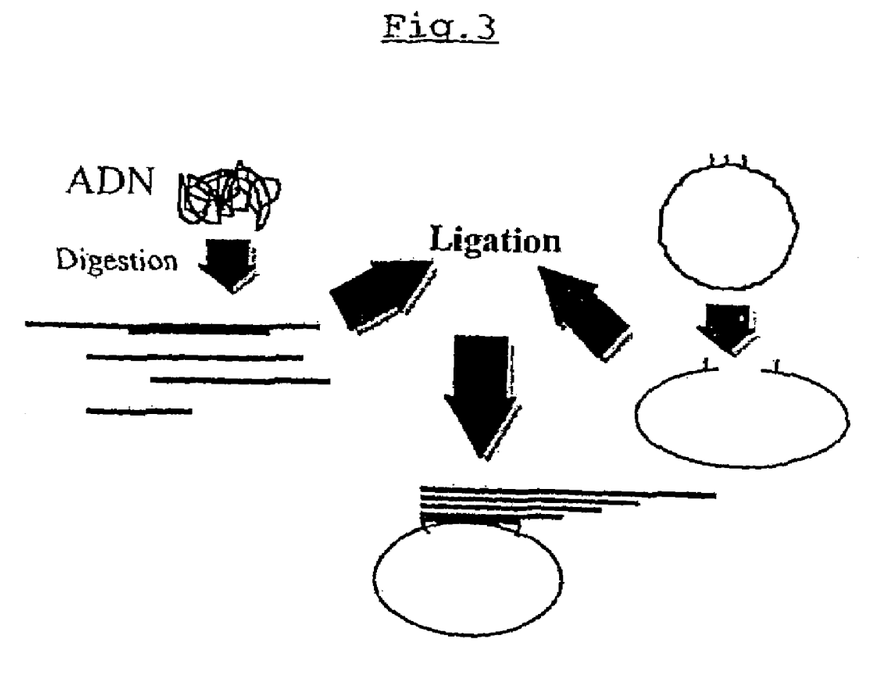
FIG. 3 is a schematic representation of the application of the process of the invention to Southern Blot identification.

For the application of the process of the invention to Southern Blot identification and to the study of polymorphism, there was prepared, as shown schematically in attached FIG. 3, a genomic DNA library of $4 \cdot 10^6$ different fragments, each of 1 kb. This library was obtained by using an enzyme corresponding to a site of a theoretical frequency of 1/1024 (of type AT(ACGT) (TGCA) TA).

All types of DNA libraries, such as those obtained by random PCR amplification using degenerated or non-degenerated oligonucleotides, are included within the scope of the present invention.

The invention therefore has as its object a process for cloning a nucleic acid fragment comprising the following steps:
  a library of DNA capable of containing said fragment is prepared,
  said library is screened using in a combinatory manner at least 10 and preferably 50 to 70 restriction enzymes in order to isolate by all suitable means the clone containing said fragment.

In this process, the preparation of the library of DNA capable of containing the nucleic acid fragment consists of inserting each of the DNA fragments from a sample in a vector free of all restriction enzyme cleavage sites with the exception of:
  one site for the construction of the library, and
  possibly two other identical sites, which are different from the first site(s) and flank it or them, which are useful for subcloning the nucleic acid sequence once it has been identified and, cloned.

In another form of implementation of this process, each of the DNA fragments from a sample is inserted in a vector that is substantially free of restriction enzyme cleavage sites with, the exception of:
  two sites for the construction of the oriented library, and
  possibly two other sites which can be identical or different from each other, and which are different from the two first sites and flank it or them, which are useful for subcloning the nucleic acid sequence once it has been identified and cloned.

More specifically, the process comprises the following steps:

a) A DNA library is prepared which is capable of containing said nucleic acid fragment, consisting of inserting each of the DNA fragments from a sample in a vector which is substantially free of all restriction enzyme cleavage sites but which conserves:
   one or two sites for construction of the library, and
   possibly at least two other sites, and preferably only two sites, which are identical to each other or different, but which are different from the first site(s) and flank it or them, which are useful for subcloning the nucleic acid fragment once it has been identified and cloned.

The sample from which the fragments constituting the library originate can be any eukaryote cell (mammal, plant, yeast, etc.) or any prokaryote organism (virus, bacteria, etc.). It can be genomic DNA, complementary DNA, PCR amplification fragments or any other DNA library capable of being prepared by an expert in the field.

b) Parallel digestion of the library is implemented with a multiplicity of restriction enzymes, at least 10 and preferably 50 to 70 restriction enzymes, so as to obtain a number of monodigested libraries corresponding to the number of enzymes employed.

c) The monodigested libraries are transfected in suitable cellular hosts so as to obtain corresponding lots of cellular hosts.

d) Using any suitable means, the lots obtained in step c) are tested to evaluate the integrity of the nucleic acid sequence to be cloned and thereby establish its MEC.

Thus, if digestion by an enzyme designated "I" does not alter the integrity of the insert present in the library, the insert is considered to be $I^r$, whereas if it is altered, the insert is considered to be $I^s$.

Steps a) to d) above allow analysis of the fragment to be cloned according to the invention.

The process of the invention also comprises the following steps which allow purification of the fragment to be cloned:

e) The total library from step a) is taken up again and digested essentially simultaneously by the enzymes that do not affect the integrity of the fragment to be cloned, i.e., those which were considered to be "r".

f) The resistant clone containing the nucleic acid fragment to be cloned is isolated by any suitable means and it is possibly subcloned using the two sites provided in the vector for that purpose.

g) The nucleic acid fragment to be cloned is possibly sequenced.

The multiple digestion of step e) has the effect of cleaving the totality—or almost the totality—of the DNA fragments constituting the library, with the exception of the fragment to be cloned.

Isolation of the resistant clone containing the nucleic acid fragment to be cloned from step (f) can be performed by transformation of the multidigested library in competent bacteria, or by PCR using the primer oligonucleotides flanking the library cloning site.

Possibly, for security one can perform the verification steps between steps a) and b), on the one hand, and e) and f), on the other hand, consisting of:

a') Verifying the presence in the library of the nucleic acid fragment to be cloned by transfecting in a cellular host which does not have said fragment and testing by any suitable means for the presence of the fragment in said host. COS cells, which are conventionally employed for transfections, are advantageously used in this step a').

e') Transforming the multidigested library of step e) in competent hosts so as to verify the nature of the cloned fragments. For example, this step consists of spreading on a Petri dish and then verifying by plasmidic DNA minipreparations (minipreps) that the inserts are truly sensitive to the enzymes recorded as "s) during the establishment of the MEC.

The DNA library prepared in step a) advantageously contains from 1 to $10^8$, and preferably on the order of $10^5$ to $4 \cdot 10^6$ different fragments, each on the order of 0.1 kb to 5 kb, preferably on the order of 1 to 2 kb.

In the process of the invention, it is preferable that the two subcloning sites are octonucleotidic sites, so as to minimize the risk that B sites could be present in the cloned inserts.

In a very specialized mode of implementation of the process of the invention, the library no longer contains single self-closed vectors. It is thus advantageous if the vector of the invention contains a system which eliminates single self-closed vectors, such as a suicide gene, a lambda promoter proximity disruption system or any other system known by the expert in the field.

The tests performed in steps d) and a') to verify the integrity of the nucleic acid sequence to be cloned can be any means for demonstrating either the sequence itself, such as a probe, or the protein coded by said sequence, such as a ligand, e.g., an antibody, or the activity of this protein, such as an enzymatic marker, which can be detected by any means known by the expert in the field, such as fluorescent or radioactive tagging.

The applications of the cloning process according to the invention are very numerous and especially those presented in detail in the examples below can be cited:
   Cloning of a gene by expression library.
   Cloning by homology.
   Southern blot identification, referred to by the inventor as "Identiblot".
   Study of polymorphism.

Thus, no distinction will be made below between gene or insert or sequence with regard to the nucleic acid fragment to be cloned according to the process of the invention described below.

An expression library cloning process for a gene according to the invention comprises the following steps:

a) A cDNA library capable of containing said gene is prepared by inserting said library in a vector which is substantially free of all restriction enzyme cleavage sites but which conserves:
   one or two sites for construction of the library, and
   possibly at least two other sites, and preferably only two sites, which can be identical or different, but which are different from the first site(s) and flank it or them, which are useful for subcloning the gene once it has been identified and cloned.

b) The presence of the target gene in the library is verified by transfecting in a cell line which does not have the target activity or phenotype and by measuring its restoration by means of a technique allowing distinction between the transfected cells and the non-transfected cells, for example by means of a cytometric or enzymatic test.

c) The library is digested independently by at least 10 and preferably 50 to 70 restriction enzymes.

d) The monodigested libraries of step c) are transfected independently.

e) Each of the lots obtained from step d) is tested by any suitable means for the presence of the activity associated with the gene to be cloned and the integrity of the sequence of said gene is evaluated in order to establish the MEC of the activity associated with said gene.

The term activity associated with the gene is understood to mean the detection by any means of the protein coded by said gene or the activity of this protein whatever it might be (ligand, enzyme, tumor inducer, etc.).

f) The total library from step a) is taken up again and digested essentially simultaneously by the 50 to 55 enzymes which, on average, do not affect the activity measured in step e). Therefore, statistically, all of the fragments constituting the library will be cleaved with the exception of the target fragment.

g) The multidigested library is transformed in competent bacteria. Therefore, only the vectors containing an uncleaved fragment will be transformed in the competent bacteria.

h) Subcloning is performed, using the enzyme(s) corresponding to the subcloning site(s) provided in the vector, and then possibly the gene is sequenced.

The invention also pertains to the monodigested or multidigested libraries obtained in the process of the invention and especially in steps c) and f) of the processes above, as well as the supports, such as the tubes, membranes, plates, gels, etc., which can contain said libraries, their expression product or the hosts containing them.

The invention also pertains to the cellular or bacterial hosts containing the aforementioned libraries.

A cloning process using homology according to the invention comprises the following steps:
  a) A cDNA library is prepared as described in step a) above.
  b) The library is digested independently by each of at least 10 and preferably circa 70 restriction enzymes.
  c) The products of the digestion of step b) are transformed in competent bacteria.
  d) The transformed bacteria are cultured in a selective medium so as to produce digested libraries free of cleaved products.
  e) Each of these libraries is cleaved separately by the enzyme(s) corresponding to the subcloning site(s) provided in the vector and each of these products is deposited separately in an agar gel or acrylamide well.
  f) The digestion products from step e) are migrated and then transferred onto a membrane, for example, a nitrocellulose membrane, and then hybridized with a specific probe of the gene to be cloned by homology, or the products from step d) are deposited directly on a nitrocellulose membrane.
  g) The MEC of the signal is analyzed.
  h) The corresponding multidigestions are implemented such that the only resistant clone is the vector carrying the gene to be cloned.

The homology cloning process described above can be applied to the identification:
  a) of alleles of different strains of animals of the same species, or of different individual humans (often very homologous).
  b) of genetic equivalents present in different species (moderately homologous).
  c) of alternative splicings of the same gene within the same tissue or between different tissues (total homology by sections).
  d) of different members of a genetic family, distributed within the same tissue or in different tissues (unpredictable homology, often very strong in certain domains).

The simplified version of this process consists of implementing dots rather than Blots, i.e., of refraining from cleaving the monodigested libraries by the enzyme corresponding to the subcloning site provided in the vector, and of depositing them directly at one point on a nitrocellulose membrane.

A Southern blot insert identification process according to the invention allows identification of a DNA fragment without having to sequence it even partially. The process comprises the following steps:
  a) A DNA library capable of containing said insert is prepared, consisting of inserting each of the DNA fragments from a sample into a vector substantially free of any restriction enzyme cleavage sites but conserving:
    one or two sites for the construction of the library, and
    possibly at least two other sites, and preferably only two sites, which are identical or different from the first site(s) and flank it or them, which are useful for subcloning the insert once it has been identified and cloned.
  b) This library is digested by each of at least 10 and preferably circa 50 to 70 restriction enzymes.
  c) The monodigested libraries obtained in step b) above are transformed in competent bacteria or equivalent hosts.
  d) The bacteria are cultured in a selective medium, so as to produce monodigested libraries that are free from cleaved products.
  e) Each of these libraries is cleaved separately by the enzyme corresponding to the two other sites which are identical or different from the first site(s) and flank it or them, and the digestion products are deposited in agarose gel or acrylamide wells.
  f) This gel is migrated and transferred onto a membrane, for example, a nitrocellulose membrane.
  g) The inserts to be identified are used like marked probes, either one by one, or several at a time.
  h) Each of the lots obtained in step g) is tested by any suitable means to associate the inserts to be identified with an MEC. This MEC corresponds to the action of the enzymes from step b).

A polymorphism study process according to the invention is identical to the Southern blot insert identification process but it is characterized in that:
  The genomic DNA library of step a) stems from the subject under study, for example a patient, or subjects from the patient's family.
  The inserts used as probes are the previously described polymorphism markers.

The applications of the polymorphism study process according to the invention are found in the context of the investigation of polymorphism markers associated with a disease and in the context of diagnosis of this disease.

A variant of the preceding cloning process for the study of the polymorphism of an individual comprises the following steps:
  a) The MEC of each of the known markers is defined so as to enable their identification.
  b) A genomic DNA library is constituted for the subject under study, consisting of inserting each of the DNA fragments from a sample in a vector substantially free from all restriction enzyme cleavage sites but conserving:
one or two sites for construction of the library, and possibly at least two other sites, and preferably only two sites, which are identical or different, and different from the first site(s) and flanking it or them, which are useful for subcloning the insert once it has been identified and cloned.

c) Digestion of the library is performed using batteries of enzymes corresponding to the MECs attributed to the markers studied.

d) The multidigested libraries are transformed in competent bacteria.

e) The bacteria are cultured in a liquid or solid medium containing the selective agent of the plasmid. If the targeted allele exists, the bacteria grow; in contrast, if this allele does not exist, the bacteria do not grow and thus one obtains a profile for each allele.

In step b), it is advantageous to prepare a library the fragments of which have an average length of 1000 to 4000, and preferably 2000 nucleotides.

One mode of implementation of the aforementioned variant also enables detection of numerous alleles of polymorphic segments, such as, for example, the gp120 of the HIV virus or the p53 of cellular oncogenes, in the context of research or diagnostics. The relevant segment is advantageously amplified by PCR and cloned in the plasmid; the process is then identical to that described above and presented in detail in example 6 below.

The invention also has as its object a mixture of at least 10 and preferably 50 to 70 restriction enzymes capable of being used in a process according to the invention.

The invention also pertains to the use of a vector substantially free of any restriction enzyme cleavage sites but conserving:
one or two sites for construction of a library, and
possibly at least two other sites, and preferably only two sites, which are identical or different, and are different from the first site(s) and flank it or them, which are useful for subcloning the fragments in said library,
for screening a DNA library.

Thus, the invention also has as its object a nucleic acid library cloned in a vector, capable of being prepared in a process as described above, characterized in that said vector is substantially free of any restriction enzyme cleavage sites but conserves:
one or two sites for construction of the library, and
possibly at least two other sites, and preferably only two sites, which are identical or different, and are different from the first site(s) and flank it or them, which are useful for subcloning the fragments of the library.

Said vector advantageously carries a system that eliminates any single self-closed vectors.

The invention also relates to:
a library of DNA multidigested by a previously described mixture of enzymes,
a group of DNA libraries in which each library is monodigested independently by each of the enzymes of the previously described mixture of enzymes,
as well as the cellular or bacterial hosts or supports containing a library or a group of the above libraries.

Other advantages and characteristics of the process of the invention will become apparent from the description below which relates to the detailed examples of implementation of the process of the invention in various applications which should not be considered to comprise limitations in any manner of the invention.

EXAMPLE 1

Preparation and Exploitation of an Expression Library

A first application of the process of the invention relates to the preparation and exploitation of an expression library.

There has been great interest in this technique since the 1980s. Numerous genes, such as those coding for the cytokine receptors, the lymphocyte surface markers, the proteins binding DNA, etc., have been identified by this technique (U. Gubler et al., Annals of the N.Y. Academy of Science 795: 36–40, 1996; D. Pennica et al. PNAS 92(4): 1142, 1995; R. M. O'Brien et al., Biochemical Journal 312: 17–21, 1995). However, these expression library cloning techniques still remain time consuming and poorly reproducible.

The present applications of expression libraries pertain to the identification of the gene coding for a protein, of which the means for demonstrating this can be grouped into four principal categories:
the antibodies,
the protein/protein bonds other than antibody/antigen bonds,
the oligonucleotides marked by, for example, fluorescence in the case in which the target protein is a protein binding to DNA,
the protein activity tests of all types.

The library containing the gene coding for the target protein can be transformed in bacteria or yeast, and use is made of antibodies, the protein or marked oligonucleotide for scanning the library in the research directed at the colony which expresses it. These systems often perform very poorly because the proteins do not have the same conformation and the same post-transductional modifications in the bacteria or yeast as in mammalian cells.

The problem of transfection of libraries in mammalian cells is due to the fact that, unlike the case of the bacteria or yeast systems, a multiplicity of plasmids are integrated in each cell. In order to control this problem, it is necessary to use successive fractioning techniques on the libraries or repeated tris cytofluorometric techniques (T. Kitamura et al., PNAS 92(20): 9146, 1995; D. R. Gehlert et al., Molecular Pharmacology 49(2): 224 (1996)). Both of these techniques require extensive work and time (several weeks). They are not always conclusive, nor are they suitable for the simultaneous cloning of two or more inserts.

The process of the invention is much simpler and less costly than the techniques of the prior art above. In addition, the process of the invention can be applied to the simultaneous cloning of a multiplicity of inserts. This latter point takes on great importance because it is known that many surface proteins are composed of many chains and do not reach the surface until all of the chains are produced, for example in the case of the major histocompatibility complexes. In contrast, it is not possible to gain access to these proteins by means of any of the techniques of the prior art based on expression libraries.

Figure 4:
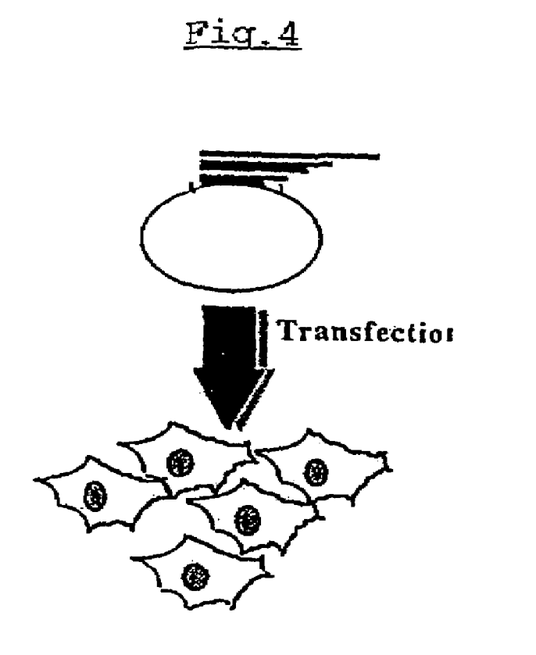
FIG. 4 is a schematic representation of the transfection of a target gene.
Figure 5:
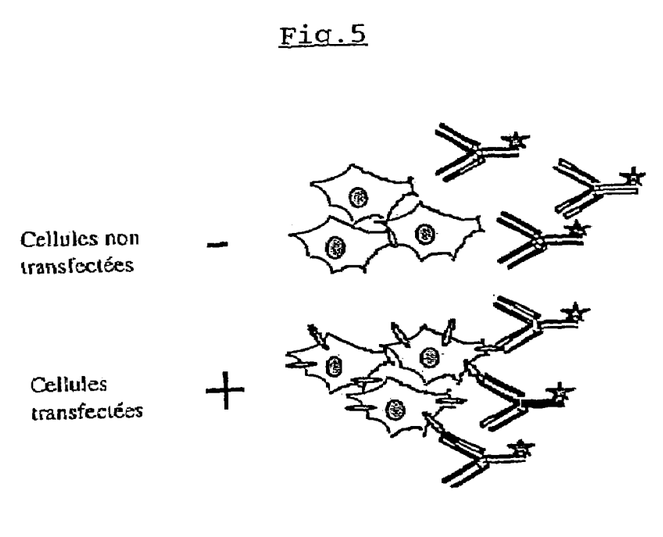
FIG. 5 is a schematic representation of screening cells to separate transfected from non-transfected cells.

A process of the invention for the constitution of expression libraries comprises the following steps:

a) A library is prepared by inserting in site A of the vector the complementary DNA of the tissue or of the cell line that is of interest. Attached FIG. 2 shows a schematic representation of this step.

b) The presence of the target gene in the library is verified by transfecting in a cell line which does not have the target activity or phenotype, and then measuring its restoration, for example with an antibody, so as to distinguish the transfected cells (+) from the non-transfected cells (−). Attached FIGS. 4 and 5 are schematic representations of this step.

Figure 6:
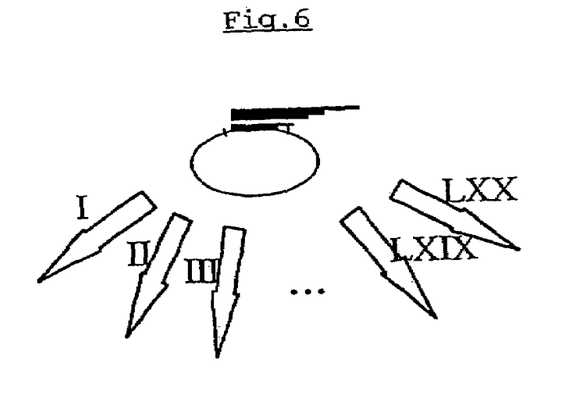
FIG. 6 is a schematic representation of the digestion of a library by 50–70 restriction enzymes.

Advantageously, use is made of COS cells, which are conventionally used for transfections.

c) The library is digested independently by each of the 50–70 available restriction enzymes. This results in 50 to 70 tubes. Attached FIG. 6 is a schematic representation of this step.

d) The 50 to 70 monodigested libraries are transfected independently, and tests are performed to determine the presence of the target activity in each of these 50 to 70 lots of transfected cells. Attached FIG. 7 is a schematic representation of this step.

e) Thus, the MEC of the target activity is established. If the digestion by the enzyme I does not alter the activity of the insert present in the library, it is recorded as $I^r$, whereas if the activity is altered it is recorded as $I^s$.

Figure 7:
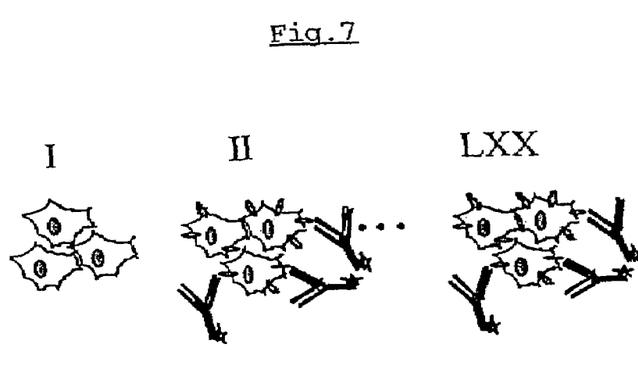
FIG. 7 is a schematic representation of libraries digested by by 50–70 restriction enzymes, then transfected.

In the example of attached FIG. 7, the following MEC is obtained: $I^s II^r \ldots LXX^r$.

Figure 8:
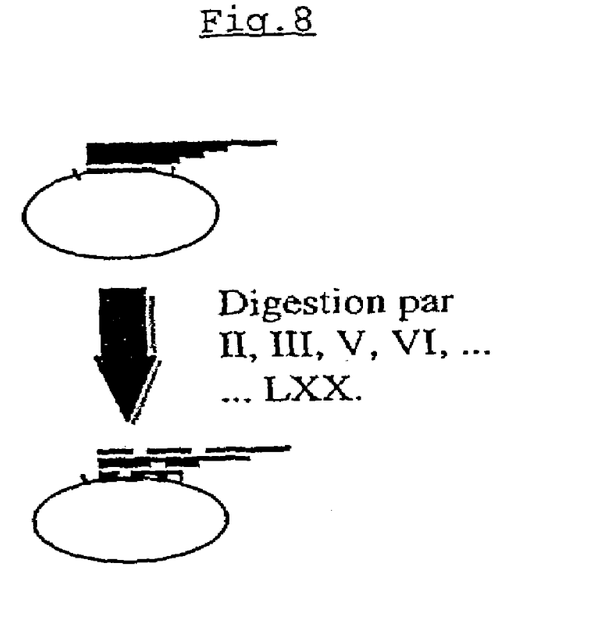
FIG. 8 is a schematic representation of the simultaneous digestion of a library by enzymes to which the target insert is not sensitive.

It is estimated that on average 55±4 enzymes out of 70 will have an r, and 15±4 will have an s for a 1-kb insert. In fact, the probability of cleavage by a restriction enzyme with a hexanuleotidic site at a given position taken at random is $p=1/4^6=1/4096$. In a gene whose size is n nucleotides, the theoretical probability of having 1, 2, 3, . . . cleavages follows a binomial law of probability p and number of events n. The probability of not having any cleavage is $C_n^0 p^n (1-p)^0$. In the case in which n=1000, the probability is 78.3%. The probability of having one or more cleavages is circa 21.7%. The mean number of enzymes not cleaving is thus 0.783×70=55, and the standard deviation is close to 4.

f) The total library is taken up again and it is digested simultaneously by the 55 enzymes which do not affect the measured activity which is associated with the "r" for the target insert. Attached FIG. 8 is a schematic representation of this step.

In practice, this digestion can not be totally simultaneous because of reasons related to buffer compatibility, such that it is necessary to perform 2 or 3 successive multidigestions corresponding to the two or three buffers selected.

The probability for a randomly selected insert to be cleaved by x of these 55 enzymes also follows a binomial law, with a probability of 0.783 and a number of events 55. Thus, the probability for an insert to not be cleaved by any of the 55 enzymes is $C_{55}^0 \times (0.783)^{55} \times (1-0.783)^0 = (0.783)^{55} = 1.4 \cdot 10^{-6}$.

Thus on average there remains only the target insert plus $1.4 \cdot 10^{-6} \times 10^5 = 0.14$ parasite insert.

Figure 9:
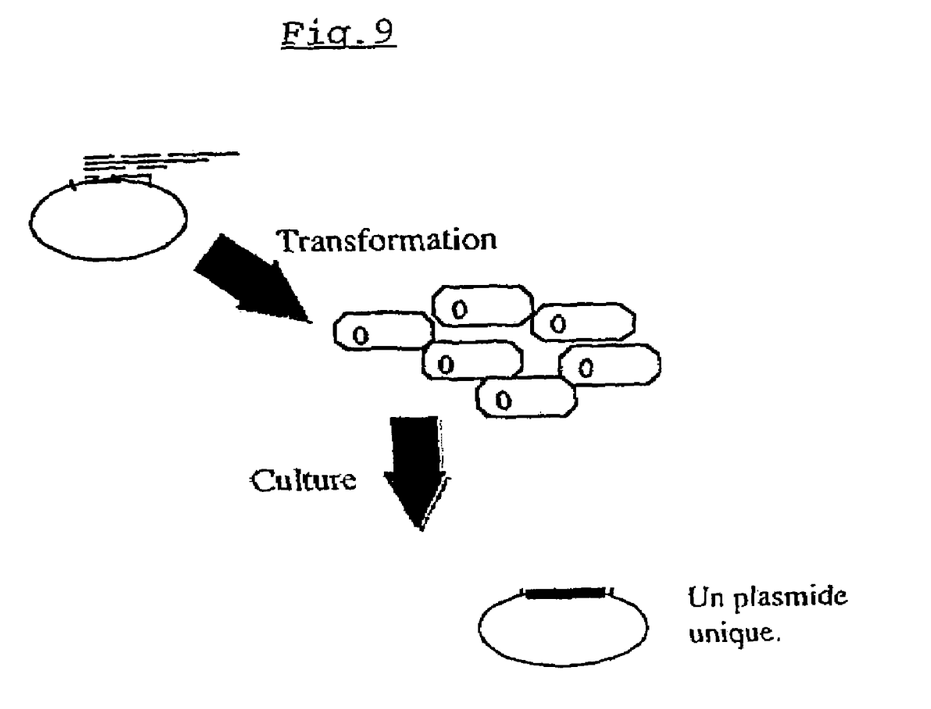
FIG. 9 is a schematic representation of the transformation of a multidigested library.

The partial use of the MEC corresponding solely to the enzymes associated with an r is sufficient for isolating the target gene, which is already pure at more than 85%.

g) The multidigested library is transformed in competent bacteria. Advantageously, spreading on petri dishes or minipreps is used to verify that the enzymes are indeed sensitive to the enzymes that were recorded as "s" during the establishment of the MEC. Attached FIG. 9 is a schematic representation of this step.

h) Subcloning is performed using enzyme B in a study vector such as Bluescript. Then, advantageously, sequencing is performed.

The model described in step e) above conforms to reality but only represents an average. In fact, the probability of cleavage varies from one enzyme of hexanucleotidic type site to another.

Each of the 8 steps requires only a short amount of time such that the above process can be performed over 16 days, of which 10 are work days.

Figure 10:
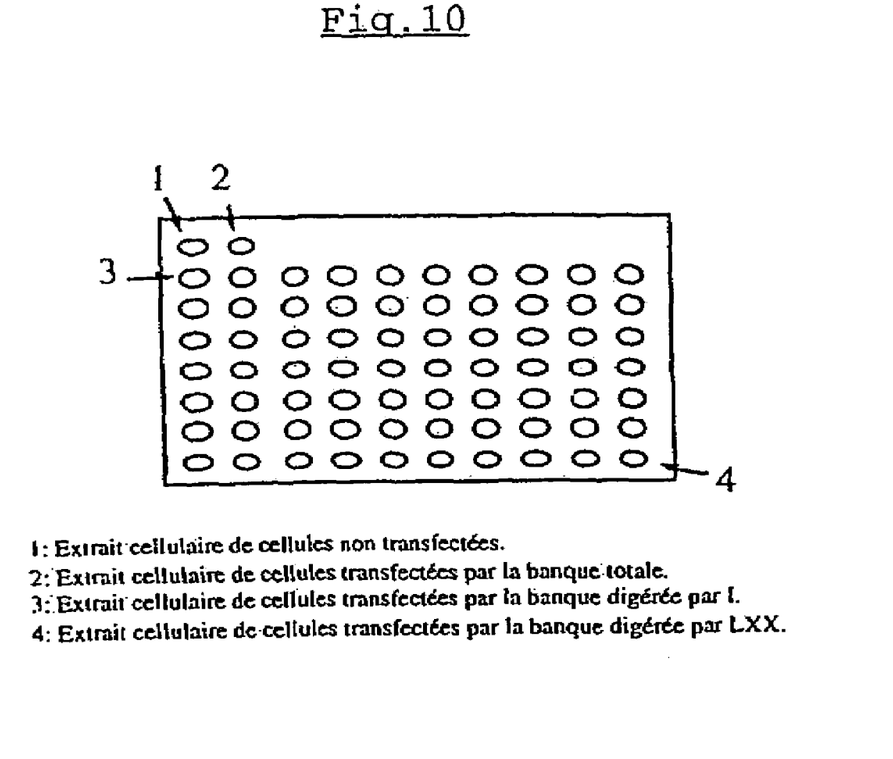
FIG. 10 is a plan view of a membrane having extracts from cells transfected with digested libraries deposited thereon.

The process of the invention enables notably generation of expression libraries for numerous tissues and lines, then performing the 50 to 70 simple digestions, transfecting them, performing cell extraction from the transfected cells and depositing them on a membrane as shown in FIG. 10.

Figure 11:
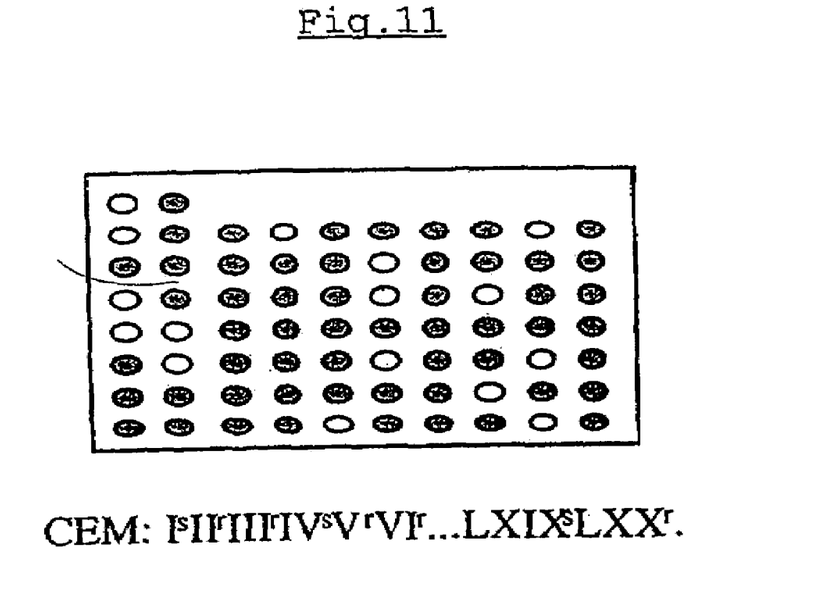
FIG. 11 is a plan view of a Western blot-developed membrane of FIG. 10.

All that remains to be done then is to develop the membrane, for example with an antibody using the Western blot technique, in order to immediately obtain the MEC of the target insert as shown in FIG. 11. The library is then multidigested as a function of the MEC obtained, then competent bacteria are transformed with this multidigested product and the gene is cloned in 3 days rather than in several months as was the case with the techniques of the prior art.

These membranes can be preserved indefinitely at 4° C. or frozen.

The example above is based on the use of a specific antibody but other development systems for the phenotype associated with the MEC can be used, such as an enzymatic test.

EXAMPLE 2

Cloning by Homology

Homology cloning is intensively used by an extremely large number of molecular biology laboratories for the identification:

a) of alleles of different strains of animals of the same species, or of different individual humans (often very homologous).

b) of genetic equivalents present in different species (moderately homologous).

c) of alternative splicings of the same gene within the same tissue or between different tissues (total homology by sections).

d) of different members of a genetic family, distributed within the same tissue or in different tissues (unpredictable homology, often very strong in certain domains).

The strategies used in the prior art are essentially the two below (M. Parmentier et al., Nature 355: 453, 1992):

PCR by homology and its derivatives, which raise the problem of the selection of primers since the conserved parts are not known. The window between the aspecific background noise and the true homologous amplifications is narrow. In addition, the amplified part most commonly does not represent the entire gene and it is therefore necessary to search for the missing pieces, and especially the part at 5', using labor-intensive techniques such as primed PCR.

Hybridization of presently existing libraries. This method is effective but requires a large amount of work. In addition, it can only be applied to the identification of alleles a) or genetic equivalents b). For the identification of alternative splicings c) or of different members of the same genetic family d), it is always necessary to redone the majority cDNA, thus in most cases, the gene which is already available.

By means of the process of the invention, once a gene has been cloned it is possible to produce a probe which hybridizes on homologous genes. Thus, this probe can be used to search for its homologues by low stringency hybridization.

Figure 12:
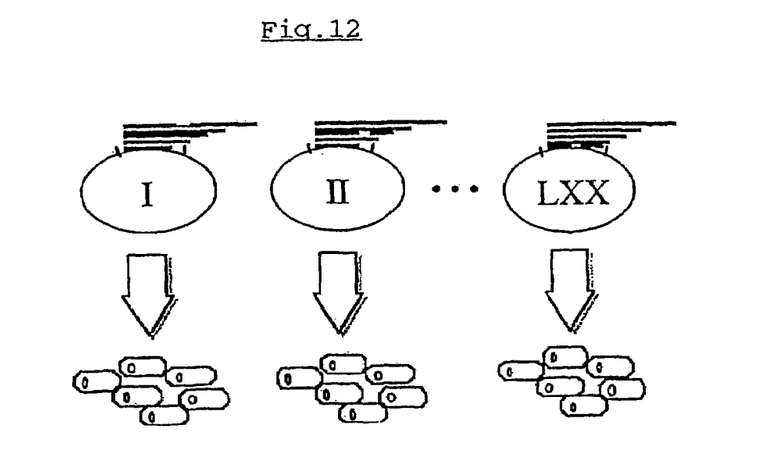
FIG. 12 is a schematic representation of the transformation of 70 digested libraries into bacteria.
Figure 13:
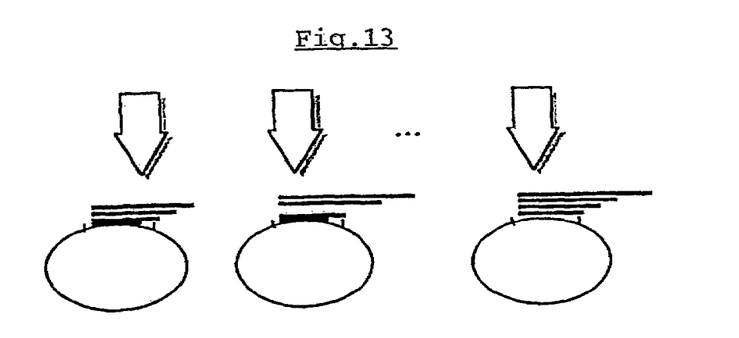
FIG. 13 is a schematic representation of libraries produced from cultured bacteria of FIG. 12.
Figure 14:
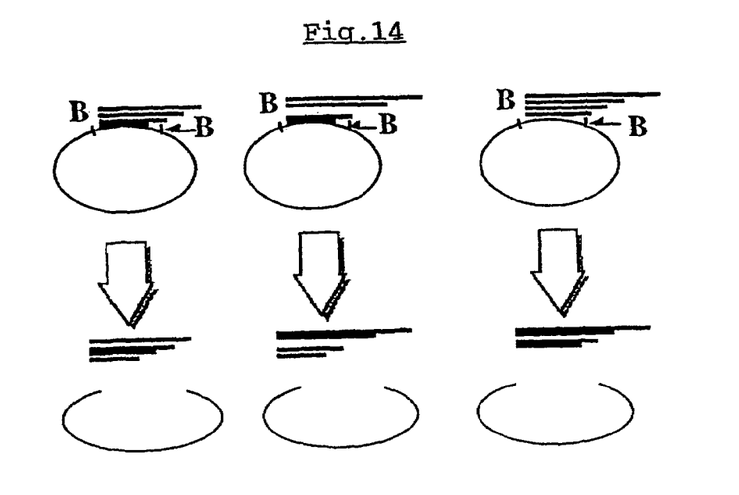
FIG. 14 is a schematic representation of the libraries of FIG. 13 after cleaving with enzyme B.

The homology cloning process according to the invention comprises the following steps:
 a) A cDNA library is prepared as in step a) of example 1.
 b) The library is digested independently by each of the 70 restriction enzymes as described in step c) of example 1.
 c) These 50 to 70 digestions are transformed in competent bacteria. Attached FIG. 12 is a schematic representation of this step.
 d) The transformed bacteria are cultured in a selective medium so as to produce large amounts of digested libraries free of cleaved products (not transforming because of their linearization). The cleaved elements are henceforth absent from the libraries. Attached FIG. 13 is a schematic representation of this step.
 e) Each of these libraries is cleaved separately by enzyme B. Attached FIG. 14 is a schematic representation of this step.

Figure 15:
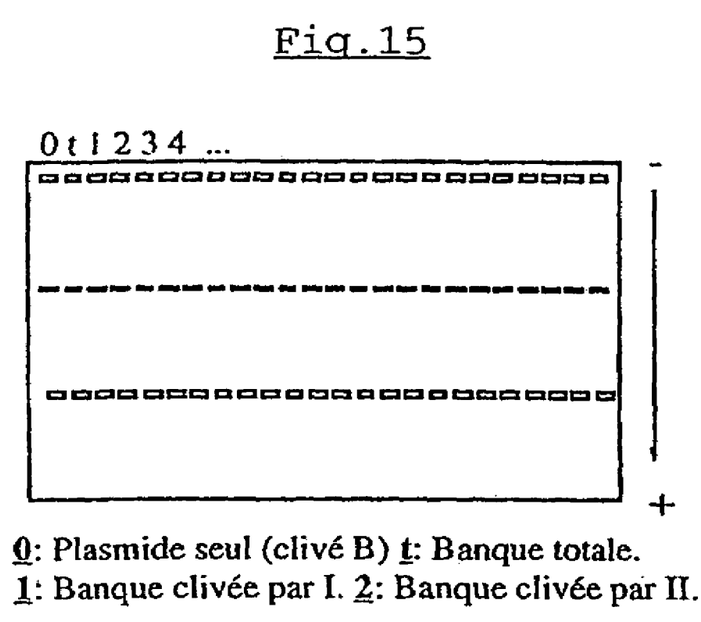
FIG. 15 is a plan view of an agarose gel well with the digestion products of FIG. 14.

Then each of these 50 to 70 digestion products is deposited separately in an agarose gel well as shown in attached FIG. 15.

Figure 16:
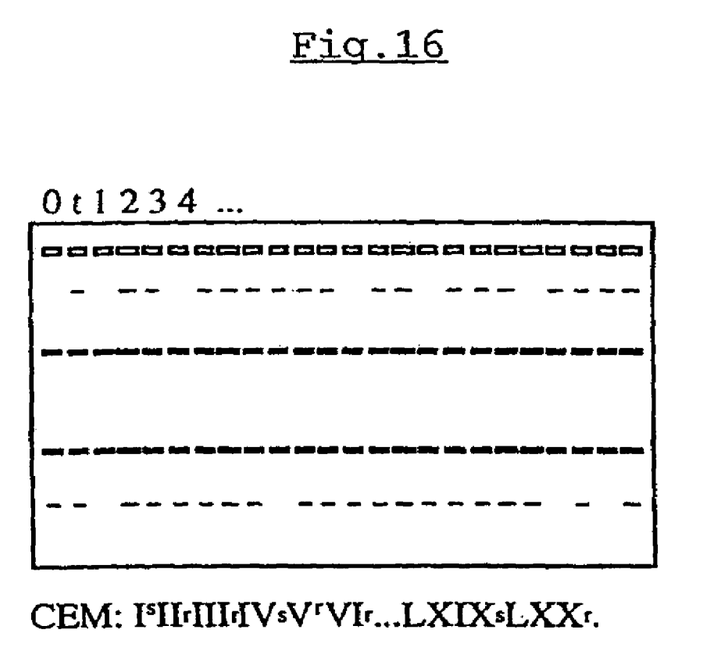
FIG. 16 is a plan view of developed membrane of the agarose gel of FIG. 15 after migration.

Then migration is implemented, transfer onto nitrocellulose and hybridization with the probe as shown in attached FIG. 16.
 f) The MEC of the signal is analyzed. Thus, if a band is present in the "non-digested library" track but absent in the "library digested by I" track, this means that the hybridized insert is sensitive to the enzyme I, and so forth.
 g) The corresponding multidigestions are performed and the sole resistant plasmid is sought. It is then advantageously possible to perform minipreps with this plasmid using the "s" enzymes for confirmation.

This process can be used industrially, by proposing the blots corresponding to numerous libraries such as those performed in example 1. Thus, having available the probe and the judiciously selected Blots, it is possible to almost immediately find all of the corresponding alleles of the species, alternative splicings and isotypes (two work days, not counting the sequencing).

Figure 17:
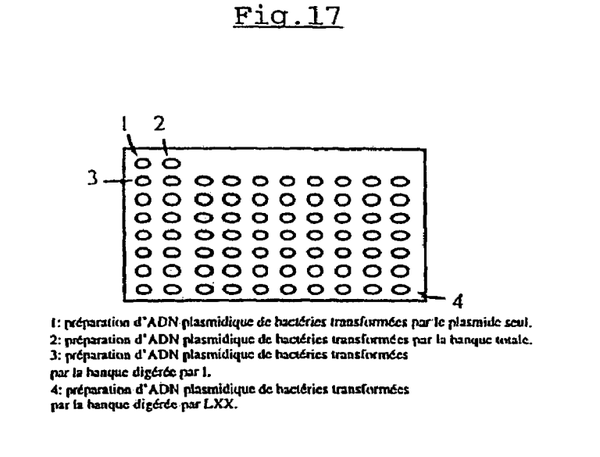
FIG. 17 is a plan view of monodigested libraries deposited on a nitrocellulose membrane.
Figure 18:
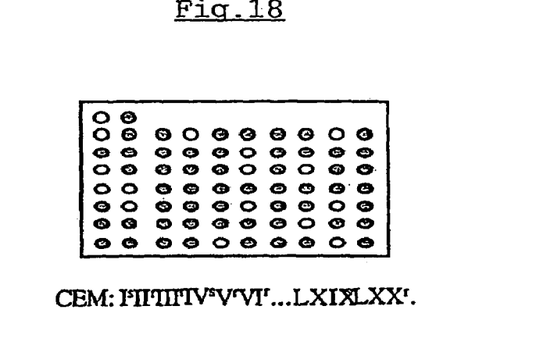
FIG. 18 is a plan view of the membrane of FIG. 17 after developing with a labeled probe.

A simplified version of this process consists of performing Dots rather Blots, i.e., of refraining from cleaving the monodigested libraries by enzyme B, and of depositing them directly on a point on a nitrocellulose membrane. Upon hybridization with the probe, the points generating a signal, for example a radioactive signal, will correspond to the enzymes for which the plasmid would be resistant. Those points no longer retaining a signal would correspond to the enzymes for which the insert is sensitive. Thus, the analysis is close to that developed in example 1, as shown in attached FIGS. 17 and 18.

This simplified version, however, is insufficient for cloning isotypes or alternative splicings expressed in the same cell.

EXAMPLE 3

Southern blot "Identiblot" identification

The preceding applications of the process of the invention are intended to simplify and decrease the time requirement for cloning by expression or homology by offering new possibilities.

The Southern blot identification proposes a shortcut which will simplify the work of researchers involved in molecular cloning techniques.

As is known, it occurs frequently in the prior art that a cloning strategy leads to the production of numerous inserts, among which can be found the target gene and numerous parasites. In the prior art, in order to identify an insert among all of these parasites, it is necessary to at least partially sequence it, which represents a considerable task. Sequencing is a time-consuming technique and too powerful for this simple task of insert identification, since in fact in most cases the reading of 10 nucleotides is sufficient for identifying an insert. A less powerful but less time-consuming technique, using DMD, could replace the technique of the prior art.

Thus, as described above, it is possible to perform Southern blots of genomic DNA libraries on an industrial scale. A schematic representation of the preparation of such a genomic DNA library is shown in attached FIG. 3. This Southern blot, renamed "Identiblot" in the context of the present invention, is sufficiently informative to enable identification of the DNA fragment homologous with the probe.

In fact, this Southern blot is one hundred million times too informative. The genomic library is constituted by 4 million different inserts with a length of 1 kb. For the same reasons as those presented above, an insert taken at random would be resistant to 55 out of 70 enzymes and sensitive to 15. The number of possible enzyme combinations is thus $C_{70}^{15}$, i.e. $70!/(55!15!)=7.2 \cdot 10^{14}$. This number is more than one hundred million times larger than the size of the library. The fact of considering that all of the inserts are of a different size considerably increases the possibilities. Each insert of the library is thus associated with an original MEC.

This process is of particular interest in the case of cloning strategies leading to high rates of false-positive clones, for example in the case of using subtractive libraries or insertion cloning strategies.

In fact, by starting with the fifty clones studied, it is sufficient to prepare a "multiplex probe", i.e., a common tagging of fifty inserts (in a single tube) and a single hybridization of the nitrocellulose filter. It is thereby possible to obtain the identity of the fifty inserts all at once by comparing their MECs with the EC values previously entered in a computerized database.

Figure 19:
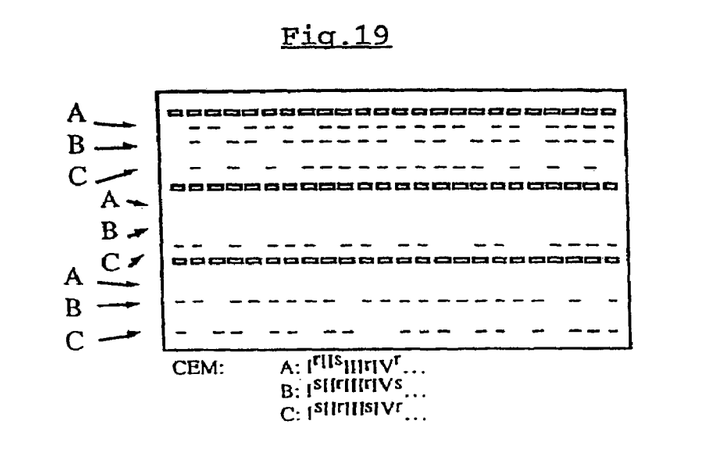
FIG. 19 is a plan view of an "identiblot" Southern blot performed with three probes.

Attached FIG. 19 shows an example in which three probes A, B and C were used simultaneously. The genomic inserts corresponding to the non-described MECs—and only those—will be cloned, for example by multidigestion, and then sequenced.

Contrary to the case of cDNA libraries, in which the variety is immense, it is sufficient to produce a single type of Blot for each of the 10 species that are currently studied in biology: human, mouse, rat, drosophila, tobacco, yeast, etc.

EXAMPLE 4

Study of Human Polymorphism

The research work performed in the context of the study of polymorphism requires the use of an increasing number of genetic markers. Their use in the context of the diagnosis of genetic diseases is also greatly increasing. It is probable that in the near future it will be possible to establish personal records indicating genetic predispositions, such that people will be able to avoid exposure to certain environmental risks, such as tobacco in the case of predisposition to lung cancer, sugar for diabetics, etc.

The techniques available in the prior art allowing the study of the polymorphism of an allele are principally PCR, Southern blot and study of the markers of satellite DNA (potentially used in combination). Thus, the method of the invention constitutes a more effective alternative to these techniques.

The implementation of the cloning process according to the invention for studying human polymorphism is close to that of example 3 above. The major difference is the fact that it is necessary to create the library, perform the digestions, the gel migration and the transfer to membrane for each subject.

This process also makes it possible to very quickly localize the origin of a genetic disease by analysis of the various members of the family harboring the disease. In a so-called "at-risk" family for a disease, all that needs to be done is to prepare the Identiblots corresponding to the different members of the family and to test them using polyprobes made from already existing genetic markers. It is possible in a single day to hybridize at least twenty membranes, i.e. to obtain the alleles from 1000 markers. Multiple genetic factors can be defined with this technique.

This application of the process of the invention requires an investment of time on the order of several hours of work, but it is quickly profitable because of the possibility of testing the genetic predispositions 50 by 50, by means of multiplex probes prepared routinely and constituted by the equivalent number of markers.

EXAMPLE 5

Second Approach to the Study of Human Polymorphism According to the Invention This second implementation of the process of the invention for the study of polymorphism concerns the application of DMD to the study of genetic markers by RFLP. The process according to the invention thus comprises the following steps:

a) The MECs of each of the known markers were defined in advance in order to allow their identification. This identification is performed once for all of them and thus a polymorphism is characterized by a variation in the MEC.

b) A genomic DNA library of the study subject is constituted in the previously described vector. As stated above, it can be advantageous if the single self-closed vectors are eliminated. Advantageously, a library the fragments of which have an average length of 2000 nucleotides is prepared.

c) Digestion of the library is implemented with batteries of enzymes corresponding to the MECs attributed to the markers studied.

Thus, for example, in the first well, one places the fifty enzymes that will digest all of the library with the exception of a first marker. In the second well, one places another battery of enzymes for a second marker, etc.

d) The multidigested libraries are transformed in competent bacteria.

e) Culturing is performed on a solid medium (petri dish) containing the selective agent of the plasmid such that if the target allele exists, the bacteria will grow. On the other hand, if this allele does not exist, the bacteria will not grow. Thus, one has available a profile for each allele and it is possible to study an unlimited number of markers all at once.

This process can be automated by preparing plates of 96 wells containing all of the enzyme mixtures; these plates are stored in the freezer. Different types of plates can be produced:

Markers distributed over the entire genome.
Markers distributed over a single chromosome.
Markers distributed over a precise region.
Markers linked to the risks of diseases.
Etc.

A fixed amount of DNA in library form is distributed into each well and then incubation is performed at 37° for the digestions. The competent bacteria are then added and the conventional transformation mechanism is employed (thermal shock, incubation without selection agent, etc.). 96 channels are taken with the pipette and deposited on a petri dish. The reading is performed visually or using a spectrophotometer.

This second approach has the advantage that it can be easily automated and when performed on a large scale, there is a very large time savings. In fact, it is necessary to test a large number of markers for each individual because the creation of the library represents an investment of effort. In addition, it makes it possible to avoid the use of radioactivity which is expensive and dangerous.

EXAMPLE 6

Third Approach to the Study of Human Polymorphism According to the Invention This variant of the study process for human polymorphism according to the invention relates to the application of DMD to the study of the different alleles of a single marker.

In the prior art, these differentiations are performed essentially by sequencing. In the near future, DNA chips (T. Pastinen et al., Genome Research 7: 606–614, 1997; J. G. Hacia et al., Nature Genetics 14: 441, 1996) will make it possible to automate these applications. These chips are particularly useful for the examination of the gp120 of the HIV virus or cellular oncogenes such as p53, which are present as numerous alleles.

In accordance with the present invention, this variant consist of defining in advance the MECs of each of the alleles of the segment being studied. This identification is performed once for all of the alleles and is limited to the alleles carrying at least one restriction site of difference. The fragment being studied is then amplified by PCR. Said fragment is cloned in the vector of the invention. This process is thus very close to that of example 5, but with a library comprising only one or two inserts corresponding to the two copies of the gene present in an individual. The remainder of the process is identical to that of example 5.

This application can be performed simultaneously on many inserts at once.

I claim:

1. A process for isolating a target nucleic acid fragment having a known characteristic, from a number of fragments comprising said target nucleic acid fragment, said process comprising:
   a) identifying a target nucleic acid fragment having a known characteristic;
   b) providing a number of nucleic acid fragments of different characteristics, which are capable of containing one or more of said target nucleic acid fragment having a known characteristic;
   c) preparing a first initial library of clones from said number of fragments using a vector containing no more than a pre-determined number of known restriction sites;
   d) subjecting said first initial library to a plurality of restriction enzymes individually wherein digestion of said library is performed in parallel by each individual restriction enzyme, to produce a group of monodigested libraries which correspond in number to the number of plurality of restriction enzymes used;
   e) screening said group of monodigested libraries individually for said known characteristic to detect the presence of said target fragment, to thereby determine those restriction enzymes to which said target fragment is insensitive;
   f) preparing a second initial library which is substantially the same as the first initial library;
   g) producing a multidigested library by digesting said second initial library with all of the plurality of restriction enzymes to which said target fragment is insensitive as determined in step e, and obtaining said multidigested library which contains the target nucleic acid fragment; and
   h) isolating said target nucleic acid fragment from the multidigested libraries.

2. The process of claim 1 wherein said plurality of restriction enzymes comprises at least 10 restriction enzymes.

3. The process of claim 1 wherein said plurality of restriction enzymes comprises at least 50 restriction enzymes.

4. The process of claim 1 wherein said plurality of restriction enzymes comprises at least 70 restriction enzymes.

5. The process of claim 1 wherein said pre-determined number of known restriction sites is four.

6. The process of claim 1 wherein said pre-determined number of known restriction sites is three.

7. The process of claim 6 wherein at least one of said three sites is different from, and flanked by, said two remaining sites.

8. The process of claim 1 wherein said restriction enzymes have cleavage sites from 5 to 6 nucleotides in length.

9. The process of claim 1 including the further step of transforming and replicating said intact clone of the target nucleic acid fragment.

10. The process of claim 9 including the further step of isolating said intact clone.

11. The process of claim 1 comprising, after step b), the further step of transfecting said monodigested libraries in cellular hosts.

12. The process of claim 1 comprising the further step of verifying the presence of said target fragment in said initial library by transfecting in a cellular host and screening said transfected host for the presence of said target fragment.

13. The process of claim 1 comprising the further step of verifying the presence of said target fragment in said multidigested library by transforming said library and screening said transformed library for the presence of said target fragment.

14. The process of claim 1 wherein said number of fragments contains up to 108 fragments, each from about 00.1 kb to 5 kb in size.

15. A process for isolating a target nucleic acid fragment having a known characteristic, from a group of fragments comprising said target nucleic acid fragment, said process comprising:
   a) identifying a target nucleic acid fragment having a known characteristic of interest;
   b) providing a number of said nucleic acid fragments of different characteristics, which are capable of containing one or more of said target nucleic acid fragments having a known characteristic;
   c) preparing first initial library of clones from said number of fragments using a vector containing no more than a pre-determined number of known restriction sites;
   d) verifying the presence of said target fragment in said initial library by transfecting in a cellular host and screening said transfected host for the presence of said target fragment;
   e) subjecting said first initial library to a plurality of restriction enzymes individually wherein digestion of said library is performed in parallel by each individual restriction enzyme, to produce a group of monodigested libraries which correspond in number to the number of plurality of restriction enzymes used;
   f) independently transfecting said monodigested libraries;
   g) screening said group of monodigested libraries for said known characteristic to detect the presence of intact target fragments, to thereby determine those restriction enzymes to which said target fragment is insensitive;
   h) preparing a second initial library which is substantially the same as said first initial library;
   i) subjecting said second initial library to all of said plurality of restriction enzymes to which said target fragment is insensitive as determined in step g, to produce a multidigested library having the target nucleic acid fragment;
   j) transforming said multidigested libraries; and
   k) isolating said target nucleic acid fragment.

16. The process of claim 15 wherein said restriction enzymes have cleavage sites from 5 nucleotides in length.

17. A process for isolating an intact clone of one a target nucleic acid fragment having a known characteristic, from a group of fragments, said method comprising:
   a) preparing first initial library of clones from said group of fragments using a vector containing no more than a predetermined number of known restriction sites;
   b) subjecting said first initial library to a plurality of restriction enzymes individually wherein digestion of said library is performed in parallel by each individual restriction enzyme, to produce a group of monodigested libraries which correspond in number to the number of plurality of restriction enzymes used;
   c) transforming said monodigested libraries into bacteria;
   d) culturing said bacteria to produce digested libraries substantially free of cleaved products, cleaving each digested library to produce digestion products, depositing said products in an agarose gel well, migrating said products, transferring said products onto a membrane, hybridizing said transferred products with a probe, to thereby determine those restriction enzymes to which said target fragment is insensitive;
e) preparing a second initial library which is the same as the first initial library;
f) subjecting said second initial library to all of said plurality of restriction enzymes to which said target fragment is insensitive as determined in step d, to produce a multi-digested library having an intact clone of the target nucleic acid fragment; and
g) isolating said target nucleic acid fragment.

18. A method for producing a group of monodigested libraries from a group of fragments, said method comprising:
a) preparing an initial library of clones from said group of fragments using a vector containing no more than a pre-determined number of known restriction sites; and
b) subjecting said initial library to a plurality of restriction enzymes individually and in parallel, to produce a group of monodigested libraries corresponding in number to the number of restriction enzymes used.

* * * * *